US010546193B2

(12) United States Patent
Schmidt et al.

(10) Patent No.: US 10,546,193 B2
(45) Date of Patent: Jan. 28, 2020

(54) METHOD AND SYSTEM TO CONTROL A WORKFLOW AND METHOD AND SYSTEM FOR PROVIDING A SET OF TASK-SPECIFIC CONTROL PARAMETERS

(71) Applicant: APPLE INC., Cupertino, CA (US)

(72) Inventors: Eberhard Schmidt, Kleinmachnow (DE); Tom Sengelaub, Berlin (DE)

(73) Assignee: APPLE INC., Cupertino, CA (US)

( * ) Notice: Subject to any disclaimer, the term of this patent is extended or adjusted under 35 U.S.C. 154(b) by 23 days.

(21) Appl. No.: 15/750,032

(22) PCT Filed: Aug. 5, 2016

(86) PCT No.: PCT/EP2016/068818
§ 371 (c)(1),
(2) Date: Feb. 2, 2018

(87) PCT Pub. No.: WO2017/025486
PCT Pub. Date: Feb. 16, 2017

(65) Prior Publication Data
US 2018/0225509 A1 Aug. 9, 2018

(30) Foreign Application Priority Data

Aug. 7, 2015 (EP) ..................... 15180283

(51) Int. Cl.
*G06K 9/00* (2006.01)
*A61B 5/16* (2006.01)
(Continued)

(52) U.S. Cl.
CPC .......... *G06K 9/00597* (2013.01); *A61B 3/113* (2013.01); *A61B 5/1128* (2013.01);
(Continued)

(58) Field of Classification Search
CPC ...... G05B 19/0426; G05B 2219/24024; G06K 9/00597; G06K 9/00671; G06K 9/00771;
(Continued)

(56) References Cited

U.S. PATENT DOCUMENTS 8,618,922 B2 * 12/2013 Debouk .............. B60W 50/038
340/439
8,988,524 B2   3/2015 Smyth
(Continued)

FOREIGN PATENT DOCUMENTS

EP       2434465 A2    3/2012

OTHER PUBLICATIONS

International Search Report for corresponding PCT/EP2016/068818 dated Jan. 30, 2017.
(Continued)

*Primary Examiner* — Brenda C Bernardi
(74) *Attorney, Agent, or Firm* — Fernando & Partners, LLP

(57) ABSTRACT

The invention relates to a system and method to control a workflow comprising at least one task to be performed by a person (P3), wherein information is provided about at least one certain object (20, 32, 36, 38) related to the at least one task of the workflow, eye data (24, 26) are captured of at least one eye of the person (P3), and in dependency of the eye data (24, 26) and the information about the at least one certain object (20, 32, 36, 38) it is checked whether at least one task condition consisting in whether the task had been performed and/or whether the task is allowed to be performed is fulfilled. The invention also relates to a system and method for providing a set of task-specific control parameters (CP).

19 Claims, 4 Drawing Sheets

Figure 1:
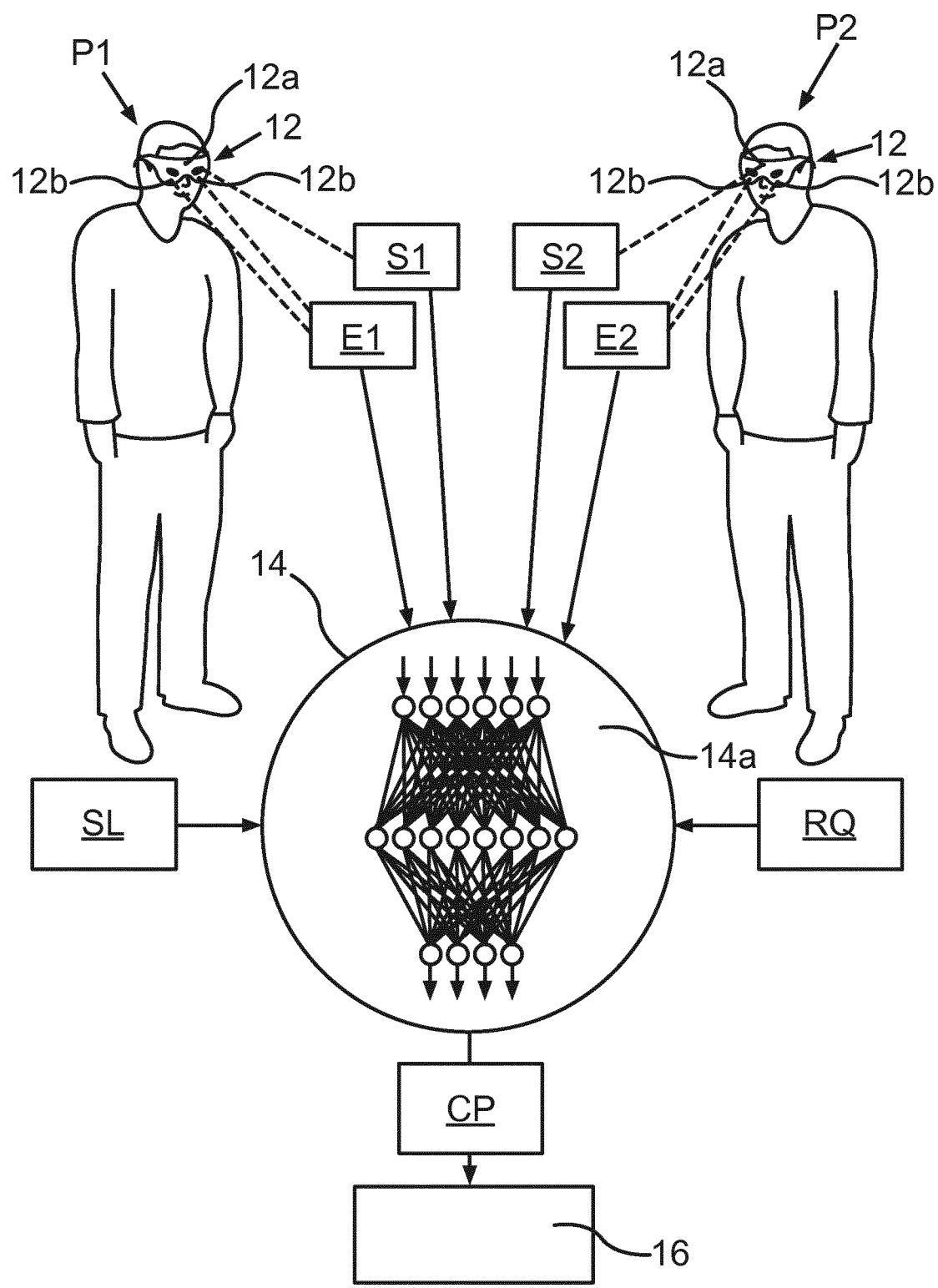

(51) Int. Cl.
*G05B 19/042* (2006.01)
*G06T 7/70* (2017.01)
*A61B 3/113* (2006.01)
*A61B 5/11* (2006.01)
*G06Q 10/06* (2012.01)

(52) U.S. Cl.
CPC .............. *A61B 5/163* (2017.08); *A61B 5/168* (2013.01); *G05B 19/0426* (2013.01); *G06K 9/00671* (2013.01); *G06Q 10/0633* (2013.01); *G06Q 10/063114* (2013.01); *G06T 7/70* (2017.01); *G05B 2219/24024* (2013.01)

(58) Field of Classification Search
CPC ....... A61B 5/1128; A61B 3/113; A61B 5/168; G06T 7/70; G06Q 10/063114; G06Q 10/0633; Y04S 10/54
See application file for complete search history.

(56) References Cited

U.S. PATENT DOCUMENTS

| | | | |
|---|---|---|---|
| 10,251,713 B2* | 4/2019 | Ruiz Morales | G06F 3/013 |
| 2006/0203197 A1 | 9/2006 | Marshall | |
| 2006/0220883 A1 | 10/2006 | Matos | |
| 2007/0291232 A1 | 12/2007 | Marshall | |
| 2010/0033333 A1 | 2/2010 | Victor et al. | |
| 2011/0111384 A1 | 5/2011 | Dietrich et al. | |
| 2011/0241862 A1* | 10/2011 | Debouk | B60W 50/038 340/439 |
| 2012/0319869 A1 | 12/2012 | Dorfmann et al. | |
| 2013/0030571 A1* | 1/2013 | Ruiz Morales | G06F 3/013 700/259 |
| 2013/0293844 A1 | 11/2013 | Gross et al. | |
| 2015/0339527 A1* | 11/2015 | Plummer | G06K 9/00845 348/78 |
| 2016/0001781 A1* | 1/2016 | Fung | B60W 40/08 701/36 |
| 2016/0318511 A1* | 11/2016 | Rangwala | B60W 50/14 |
| 2016/0375900 A1* | 12/2016 | Laur | B60W 30/09 701/41 |

OTHER PUBLICATIONS

Written Opinion for corresponding PCT/EP2016/068818 dated Aug. 4, 2017.

* cited by examiner

METHOD AND SYSTEM TO CONTROL A WORKFLOW AND METHOD AND SYSTEM FOR PROVIDING A SET OF TASK-SPECIFIC CONTROL PARAMETERS

The invention relates to a system and method to control a workflow comprising at least one task to be performed by a person, wherein information about at least one certain object related to the at least one task of the workflow is provided and eye data of at least one eye of the person are captured. The invention also relates to a system and method for providing a set of task-specific control parameters, according to which a workflow comprising at least one task to be performed by a user is controlled.

From the prior art gaze-triggered events in various contexts are known. If for example a user fixates a predefined object, then a certain action is triggered. This mechanism, however, is not embedded into a process that aims to achieve an overarching goal of the process with the related options and consequences.

Therefore, it is an object of the present invention to provide an improved system and method to control a workflow. This object is solved by a system and method with the features according to the independent claims. Advantageous embodiments of the invention are presented in the dependent claims.

According to the method to control a workflow according to the invention, the workflow comprises at least one task to be performed by a person, wherein information about at least one certain object related to the at least one task of the workflow is provided and eye data of at least one eye of the person are captured. Moreover, in dependency of the eye data and the information about the at least one certain object, it is checked whether at least one task condition consisting in whether the task had been performed and/or whether the task is allowed to be performed is fulfilled.

Advantageously, eye data of the person can be used, especially with regard to the at least one certain object to check and monitor whether single tasks of a workflow have been performed, especially correctly, or even if certain security conditions are fulfilled so that the person is allowed to perform the certain task. Therefore, the invention provides a control mechanism, which can enhance the quality of the outcome of a workflow and even reduce the risks for dangerous situations.

For example, the task can only be allowed to be performed by the person, if the person has seen and optionally acknowledged the critical information displayed, which can be derived from an analysis of the captured eye data. According to another example, if the task to be performed by the person, like a helicopter pilot, consists in scanning all instruments regularly in certain time intervals, then this can be checked on the basis of the captured eye data as well.

Advantageously, gaze data are captured as the eye data, especially a gaze direction and/or a point of the regard of the person, in particular in relation to his/her environment, especially relative to the at least one certain object. On the basis of a captured gaze direction or point of regard it can easily be checked whether the person has looked at the certain object or not, or in general on objects which are relevant for performing the task. Therefore, the use of gaze data can greatly improve a control of a workflow. Moreover, the captured eye data can also be a motion pattern relating to a motion of the at least one eye of the person and/or of at least one eye feature of the at least one eye of the person, like a pupil and/or an eyelid. On the basis of such eye motion patterns, like one or more fixations of the eye or uncoordinated eye movements, and eye feature motion like eye lid closures or the rate of eye lid closure, so called PERCLOS, and motion of the pupil like pupil contraction, advantageously much more useful information about the person can be provided, like explained in the following.

According to another advantageous embodiment of the invention a state of the person, especially an emotional state and/or a state of attention and/or a state of mind and/or a fit for duty state, is determined in dependency of the captured eye data, wherein the checking whether the at least one task condition is fulfilled is performed in dependency of the determined state. On the basis of above named motion patterns related to the motion of the eye or parts of the eye like the pupil or the eye lid, a current state of the user can be determined, which can give information about e.g. whether a user is attentive or concentrated when looking at an object or not, whether the user recognizes an object or only is looking at the object unintentionally or accidentally. Also a fit for duty state, which can be determined by fit for duty measurements, e.g. based on pupil measurements and/or eye lid closure measurements, it can be determined whether the person is tired or unfocused or not. Also the determining of the emotional state or the state of mind can be based on pupil measurements. Advantageously also states of the person can be considered when checking whether the person correctly performs a task, like when actively and concentrated looking at objects relevant for the task, or whether the person is allowed to perform the task, like when being not tired, nervous, afraid or distracted.

According to another advantageous embodiment of the invention it is classified whether the task condition is fulfilled or not by comparing a position information derived from the eye data, especially about the point of regard of the person, with a position information about the at least one certain object. On the basis of such a comparison much information about the person performing the task can be derived, for example whether the person has looked at the relevant objects for performing the task, if the person has seen the relevant information for performing a task, or to be allowed to perform the task, if the person has checked relevant objects in a predefined order, or within certain time intervals, and so on. Therefore, much information can be derived about whether the person is performing the task correctly or not or whether a person has gathered enough information to be allowed to perform the task.

Therefore, it is an advantageous embodiment of the invention that it is classified whether the task condition is fulfilled or not according to at least one classification condition consisting in that the task condition is classified as to be fulfilled, if it is detected on the basis of the eye data that the person has looked at and/or acknowledged the at least one certain object and/or has looked at and/or acknowledged a plurality of certain objects, one of which is the at least one certain object, and/or had looked at and/or acknowledged a plurality of certain objects, one of which is the at least one certain object, in a predefined timely order, and/or had looked at and/or acknowledged the at least one certain object within a predefined time interval, or regularly within predefined time intervals.

These classification conditions are very suitable for deciding, whether a task has been performed correctly or if the person has undertaken the necessary steps or read the necessary information to be allowed to perform the task. Furthermore, whether the person has not only looked at an object but also has acknowledged this object when looking at it, can be determined on the basis of above named motion pattern.

According to another embodiment of the invention it is classified whether the task condition is fulfilled or not according to at least one second classification condition consisting in that the task condition is classified as to be fulfilled if it is detected on the basis of the eye data and a comparison of the eye data with stored eye data that the person is an authorized person for performing the task. Therefore advantageously the person can be identified on the basis of the captured eye data, which can be checked against a data base to determine if the person, e.g. a worker, has a license or a required skill level or other kind of authorization e.g. to operate a chainsaw, or in general to perform the task.

Moreover, as already mentioned, further criterial relating to the state of the person, like a state of mind or a state of attention can be applied for classifying whether the task condition is fulfilled or not. Therefore, according to another advantageous embodiment of the invention, it is classified whether the task condition is fulfilled or not according to at least one classification condition consisting in that the task condition is classified as to be fulfilled, if it is detected in dependency of the determined state of the person that the person is attentive, especially when looking at the at least one certain object and/or at a plurality of certain objects, one of which is the at least one certain object, and/or at a plurality of certain objects, one of which is the at least one certain object, in a predefined timely order, and/or at the at least one certain object within a predefined time interval, or regularly within predefined time intervals. E.g. when the eye performs one or more fixations on the certain object it can be determined that the person is attentive when looking at the certain object. Also when it is determined, e.g. on the basis of eye lid closure patterns, that the person is not tired when looking at the certain object, it can be determined that the person is attentive when looking at the certain object.

In particular, the at least one classification condition is specified in dependency of the kind of the task to be performed by the person. Advantageously, suitable classification conditions can be chosen in dependency of the task to be performed by the person. This way, for each task of a workflow or also of different workflows one or more of above-named classification conditions can be specified, and maybe saved to a storage device, and which are suitable for assessing whether a task had been performed correctly and/or whether the task should be allowed to be performed or not and/or how the user did the task and/or which eye data the user produced while doing the task.

According to an advantageous embodiment of the invention the at least one certain object is an object in the environment of the person. For example, this certain object may be an object the task has to be performed with, like a device or work tool. The certain object in the environment can also be an object that provides information to the person and, at which the person has to look to perform the task correctly, like the display of a luggage scanner or also a certain display part of the display, instruments in the cockpit of an aircraft or instruments on a control panel, a medical image like a mammographic x-ray image, and so on. Therefore, many tasks involving certain objects can be assessed according to whether they have been performed by the person or not.

According to another advantageous embodiment of the invention images of the environment of the person are captured and the at least one certain object is identified in at least one of the images, especially wherein the information about a position of the at least one certain object from the at least one image is derived. The images can be captured for example by means of a camera, preferably a head-mounted camera, which can capture images of the environment of a person while the person is performing the task. The captured images can be processed and analyzed for the purpose of checking whether the person is looking at one or more predefined certain objects or not. If for example the certain object cannot be identified in one of the captured images, e.g. by means of known object recognition methods or algorithms, while the person is performing the task, then it can be concluded that the person had not performed the task correctly. Moreover, if the at least one certain object is identified in one of the images, the position of the object can be compared with a gaze direction of the person to check whether the person is looking at the certain object or not when performing the task. If not, again it can be concluded that the person may not performed the task correctly. Moreover, the image of the environment may also be used to map a user's gaze data to a specific location and to aggregate it over the time a user is performing a task e.g. if a user is performing a visual inspection of a part, the users gaze mapped to the object in a previously captured image, aggregated over the checking period may be stored as documentation of such task executed by such user.

A further great advantage is, that the system for performing the method according to the invention and its embodiments can be provided as a head-mounted device, for example having a scene camera for capturing the images of the environment of the person, as well as an eye-tracker for tracking the gaze direction of the person. Such a head-mounted system provides a lot of flexibility as it can be used in every kind of environment and for every kind of task. However, the system can also be provided as a remote system not worn by the person or attached to be person, as well. This can be very advantageous if the at least one certain object or other certain objects relating to the task are fixed in their position, like instruments of a cockpit, so that the gaze direction of a person can be captured by means of a remote eye-tracker in the position of the certain object are known to the system so that the system only has to compare the current point of regard of the user with the positions of the predefined certain objects to be able to assess whether the user looks at those objects or not.

According to another advantageous embodiment of the invention a display of a task information about the at least one task to be performed is displayed, especially by means of a display device, wherein the display of the task information is the at least one certain object. This way it can advantageously be checked whether a person has read or seen the information relating to the task to be performed in advance of performing the task so that on the basis of this information it can be assessed whether the task is allowed to be performed or not.

Therefore, in dependency of the captured gaze data it can be checked whether the person has seen and/or read task information, especially again by comparing the position of the gaze point of the person with a position of the displayed task information. So the person might only be allowed to perform the task if the person has read or seen the task information. By this embodiment a high degree of safety can be established when controlling the workflow. Also guidance for the person can be provided by means of the task information telling how the task has to be performed. Such task information can be displayed on a normal display, like a computer display or even by means of a head-mounted display.

Preferably, the task information is a warning information and/or information or instruction about how to perform the task and/or information specifying the task to be performed and/or an optical indication of an object, which is relevant for performing the task in the environment of the person. A warning information can for example provide safety instructions, the person has to read before he is allowed to perform the task. Task information can also specify the task to be performed or also how to perform the task, like a description of single steps to be performed by the person, and again only if the person has read these instructions or noticed/acknowledged the information then he is allowed to perform the task. Also objects in the environment of the person can be optically marked by means for the displayed task information, e.g. displayed by means of an augmented reality device like augmented reality glasses. Also this can give guidance to the person and may force the person to notice objects in the environment, which are important for performing the task correctly. If for example the person has to tighten several bolts in a predefined order, the task information can optically mark, e. g. by means of a head-mounted display, or augmented reality glasses, the first bolt, after that the second one, and so on, to show the person in what order the bolts have to be tightened. At the same time, the system can check, whether the person has performed the task correctly. If the person has looked at all of these bolts in the correct order, then it can be assumed, that the task was performed correctly, and otherwise, if for example the person forgot to look at one of the bolts, it can be assumed that the task was not performed correctly. In case of a visual inspection task were the order of checking operations may not be relevant the invention is very advantageous by providing guidance to the user e.g. by visually marking all still to be checked components and removing such marking after the system detected a check e.g. when the user gazed at such part.

By means of such task information it is possible to provide safety information on the one hand as well as guidance on the other hand. This way, augmented reality systems could also be advantageously used to help untrained personal to do tasks which used to require a professional, with enforcing certain sequences and/or coverage of visual intake. This can be realized safely and with less liability.

According to another advantageous embodiment of the invention, if the task condition is not fulfilled, as at least one first consequence a subsequent task of the workflow is prohibited or blocked to be performed; and/or the at least one task is not allowed to be performed; and/or information about the task condition being not fulfilled is stored and/or transmitted, e.g. to another device like that of a supervisor; and/or a warning information is outputted, especially to the person; and/or a device for performing the at least one task or a function of the device is blocked or disabled; and/or a device for performing a subsequent task of the workflow or a function of the device is blocked or disabled; and/or an output of a result of the at least one task of the workflow is blocked.

These first consequences might again depend on the task to be performed. In general, it is very advantageous to output a warning information to the person so that the person can be informed that the task he/she had to perform was not performed correctly or completely or that conditions that have to be fulfilled for performing a task, like reading the safety instructions, are not fulfilled. Also it is very advantageous to store information about the task condition being not fulfilled, which highly facilitates error tracing. Moreover, if the task condition consists in whether the task is allowed to be performed or not, it is advantageous that the at least one task is not allowed to be performed if the task condition is not fulfilled. This can be done for example if the system for performing the method according to the invention or its embodiments as coupled to a device for performing the task, in this case, a function of the device itself can be blocked or disabled so that the task cannot be performed. Even if the person already had performed the task, but did not do this correctly, in the same way a subsequent task of the workflow can be prohibited or blocked to be performed.

Similarly, according to another embodiment of the invention, if the task condition is fulfilled, as at least one second consequence a performing of the at least one task is allowed; and/or a performing of a subsequent task of the workflow is allowed; and/or a positive feedback information is outputted to the person; and/or a device for performing the at least one task or a function of the device is enabled; and/or a device for performing a subsequent task of the workflow or a function of the device is enabled; and/or a result of the at least one task or of the workflow is outputted; and/or information about the task condition being fulfilled is stored and/or transmitted.

This way advantageously the person again can be notified about the successful performance of the task, this information again can be stored and also be used as control information for controlling devices with which the task or a subsequent task has to be performed. Which of these first or second consequences is applied for a specific task again depends on the kind of task to be performed.

Therefore, it is an advantageous embodiment of the invention that for the at least one task, especially for each task of the workflow, a task-specific set of rules is specified, which define at least one of at least one classification condition, according to which it is classified whether the task condition is fulfilled or not, especially which is one or more of the above-named classification conditions, the at least one certain object, the position of the at least one certain object, the task condition, a first consequence of the task condition being not fulfilled, especially at least one of the first consequences named above, and the second consequence of the task condition being fulfilled, especially which is at least one of the second consequences named above. This way, for each task a suitable set of rules can be defined, which are then used to control the workflow, to make decision when a task is performed, performed correctly, what and which premises are made to be allowed to perform a task, and which consequences a correct or incorrect performance of a task may have.

Moreover, data relating to test persons, e.g. trained persons or professionals, performing the at least one task are collected during the test persons are performing the at least one task and the task specific set of rules is learned or derived from the collected data. This advantageous automatic learning process is explained in more detail with regard to the second aspect of this invention.

Furthermore, according to another advantageous embodiment of the invention, the eye data, in particular which are captured while the person is performing the at least one task, are stored, preferably also together with respective information about the at least one certain object, like in form of a video stream of images of the environment of the person performing the task, wherein each image contains the point of regard of the person for that point in time at which the respective image of the environment was captured. By storing these eye data or information derived from these eye data, like gaze pattern, or attention states, the whole process of preforming the task or several tasks or the whole workflow can documented, which can serve for liability purposes as well as training material for other users or for a system which can derive TC e.g. via machine learning by studying user behavior while performing a task. If the task e.g. consists in inspecting a certain component or device and a costumer owning that device then notices a failure of the device and claims that the device wasn't inspected correctly, by means of the stored eye or gaze data prove can be provided that all parts of the device have been inspected correctly and that the failure of the device is not due to a failure of inspection.

Therefore, by means of the invention and its embodiments guidelines can be established in order to ensure high quality, and especially in dangerous situations and dangerous processes to protect the worker or user. The system helps to enforce appropriate visual intake of the person to avoid critical omissions in perception or decision-making. Also, single tasks during the performance of the workflow or the performance of a whole process can be monitored individually and not only results of such a process. Often, it remains unknown which (visual) input has been missed by the person leading to an unstable process or if the intended result is not achieved the cause remains hidden. This is even more critical, when the result can be observed only a long time later or when it is too late or has become very costly to correct. This is typical e. g. in medical screening and diagnostic procedures or in preventive quality inspection task. In these cases the process itself ensures the quality as the result and their correctness can only be assessed much later, often only after irreversible damage has occurred, which should have been prevented by the diagnostic or inspection procedure in the first place. Instead, the invention manages to check single tasks and steps of a workflow with regard to their correctness so that misconduct or negligence of the person can be detected or even avoided.

The invention also relates to a system to control a workflow comprising at least one task to be performed by a person, wherein the system comprises a device for providing information about at least one certain object related to the at least one task of the workflow and a capturing device for capturing eye data of at least one eye of the person. Moreover, the system comprises a processing unit, which is configured to check whether at least one task condition consisting in whether the task had been performed and/or whether the task is allowed to be performed is fulfilled in dependency of the eye data and the information about the at least one object.

The preferred embodiments and advantages thereof described with regard to the method to control a workflow according to the invention correspondingly apply to the system according to the invention, wherein in particular the embodiments of the method according to the invention constitute further preferred embodiments of the system according to the invention. Especially, the system according to the invention is configured to perform the method to control a workflow according to the invention and/or its preferred embodiments.

Moreover, the device for providing information about the at least one certain object can be for example a camera, like a scene camera of a head-mounted device. It could also be a storage device, in which object information about the at least one certain object is stored or loaded, especially the kind and/or position of these objects. The capturing device for capturing eye data can be an eye-tracking device, like a remote eye tracker or also a head-mounted eye tracker, e. g. integrated into an augmented reality head-mounted device.

According to another aspect the invention relates to a method for providing a set of task-specific control parameters according to which a workflow comprising at least one task to be performed by a user is controlled. According to this method eye data of at least one eye of a test person are captured during the test person is performing the task. Furthermore, information about at least one visible object in the environment of the test person is provided, in which the test person is performing the task. Moreover, from the information about at least one visible object and the eye data information about the behavior of the test person performing the task with regard to the environment of the test person is derived and therefrom task-specific control parameters are derived, according to which the workflow is controlled for the user, wherein the task-specific control parameters at least specify a task condition, which specifies whether the task had been performed and/or whether the task is allowed to be performed.

This method has the great advantage that the set of task-specific control parameters, which especially can also be used for and combined with the method and system to control a workflow according to the first aspect of the invention and its embodiments, can be taught to a system automatically without having to specify these parameters manually for every single task of a workflow or also the tasks of different workflows. This way one or more test persons, like a professional, who knows how to perform the task correctly or who knows which are the necessary steps to perform the task safely, can be observed or monitored together with his/her environment when performing the task, and from this observation the task-specific control parameters can be derived to specify the task condition. So from the behavior of the test person with regard to its environment information can be derived for example like which are the relevant objects for performing the task, which is the necessary information the test person captures with his eyes, whether it is necessary to perform certain steps within time limits, or whether the timely order of performing single steps is relevant or not. All these information can advantageously be derived by comparing the gaze direction, especially the point of regard, of the test person with respect to its environment or be added manually as constraints or be learned from other parameters or be learned by how different people perform the task.

In particular, these task-specific control parameters correspond to the task-specific set or rules explained with regard to the first aspect of the invention. Therefore, according to an advantageous embodiment of the invention the task-specific control parameters specify additionally or alternatively at least one of at least one classification condition, according to which it is classified whether the task condition is fulfilled or not, and/or at least one certain object in the environment, which is classified as being a relevant object for performing the task, and/or a first consequence of the task condition being not fulfilled, and/or a second consequence of the task condition being fulfilled. Preferably, the classification condition, the certain object, the first and second consequences relate to the corresponding ones already explained with regard to the first aspect of the invention. All these parameters can advantageously be derived from the observation of the test person and its environment. Also the task-specific control parameters may specify at least one of above-named classification conditions, the certain object, first and second consequences as an alternative of specifying the task condition. Or in other words, these information can all be derived from the observation of the test person and its behavior with regard to its environment when performing the task independently from each other. Moreover, to specify the classification condition, even more useful information can be derived from the behavior of the test person with regard to the environment, like the already mentioned timely order of performing single tasks or steps of a task and whether such a timely order is relevant or not, as well as single tasks or steps have to be performed within certain time limits, regularly or not.

Furthermore, the method for providing a set of task-specific control parameters according to the second aspect of the invention and its embodiments are especially advantageous when performed on a system, which is configured as head-mounted device, e. g. with a head-mounted scene camera, for capturing images of an environment for providing information about at least an object in the environment and with an integrated eye-tracking device for capturing the eye data of the test person. By means of such a head-mounted device, it is possible that a professional simply wears this device during the performance of the at least one task wherein this device then derives from the captured information the set of task-specific control parameters, which can then be used to control the workflow comprising this task for every other user subsequently having to perform this task.

According to an advantageous embodiment the captured eye data are interpreted with regard to their relevance for the task, especially wherein a state of the person, in particular an emotional state and/or a state of attention and/or a state of mind and/or a fit for duty state, is determined in dependency of the captured eye data and used for interpreting the captured eye data. Also the task specific control parameters can be determined in dependency of the determined state of the test person. E.g. if the test person is looking at an object, but only shortly or unfocused, then therefrom the information can be derived that this object probably is not important for performing the task.

According to another advantageous embodiment of the invention, for providing the information about the at least one visible object in the environment of the test person images of the environment of the test person are captured while the test person is performing the task.

Moreover, it is preferred that the capturing of the eye data of the at least one eye of the test person as well as the providing of information about the at least one visible object in the environment of the test person are performed a plurality of times and the set of task-specific control parameters is then derived from the information about the environment provided the plurality of times and the eye data captured the plurality of times. This way the test person, like a professional, can be monitored, when performing the task a plurality of times, like hundreds or even thousands of times, and then these data can be used as described before for deriving the set of task-specific control parameters. This procedure has the great advantage that the accuracy of this method for providing the task-specific control parameters can be greatly enhanced. This way for example situations in which the test person looks at an object unintentionally and situations in which the test person looks at objects intentionally for performing the task can be distinguished with higher reliability. All these situations, in which the timely order of performing tasks or single steps, play an important role for performing the task and in which not, can be distinguished more easily. For example, if the test person is looking at several predefined objects in predefined manner, when performing the task, one cannot conclude with high reliability that this order is important for performing the task. If, however, the test person is monitored several times when performing the task, each time the test person is looking at these certain objects in the same timely order, then one can conclude with high reliability that the order is important. On the other hand, if the test person is monitored when performing the same task for several times, and each time the test person is looking at these certain objects, but not in the same timely order, then one can conclude that these objects are relevant objects, however, the order is not important for performing the task. Same applies for deriving information about time limits. Therefore, by repeating these steps several times one can gather lots of information about what are the important objects for performing a task, is the timely order of performing single steps relevant or not, are there time limits for performing single steps of the task, or the task itself, and so on with high reliability.

The repetition of the capturing and the providing a plurality of times does not necessarily have to relate to the same test person. Also different test persons can be observed and monitored when performing a task or optionally each test person can be observed or monitored a plurality of times, and then all these data, namely the eye data and the data relating to the respective environment and objects therein can be used for deriving the set of task-specific control parameters. This way also personal preferences of the test persons can be eliminated by averaging over many test persons.

According to another advantageous embodiment of the invention, the capturing of the eye data and the providing of information about the at least one visible object are performed a plurality of times for different test persons, each comprising a predefined skill level, wherein each time a result of the performance of the at least one task is assigned to a quality level, wherein the set of task-specific control parameters are additionally derived in dependency of the skill levels and quality levels. The skill levels and/or quality levels can be rated manually. The quality levels can also be rated automatically according to a suitable rating metric. The great advantage of this embodiment of the invention is that also the skill levels of the test persons performing a task as well as additionally or alternatively the qualities of the outcomes or results can be taken into consideration when deriving the set of task-specific control parameters. For example, if the test person has a high skill level, then the probability that this test person performs the task correctly is also high. Information gathered from the monitoring of this test person when performing the task can be assumed to be correct with high probability. However, if a person with low skill level performs the task, then the probability that not each step of the task or the task itself is performed correctly, can be assumed to be higher. So for example when deriving the set of task-specific control parameters from these pluralities of data sets of different persons, the data sets relating to test persons with higher skill levels can be weighted stronger with regard to their correctness. The same applies for quality levels assigned to the results of the performance of the task. If result of a performance of the task performed has a low quality, then it can be assumed that the task or at least some steps thereof were not performed correctly. If on the other hand such a result has a high quality, then it can be assumed that the tasks or all steps thereof were performed correctly, at least with high probability. Also here corresponding weights can be used for the results of different quality levels, when deriving the set of task-specific control parameters.

According to another advantageous embodiment of the invention the capturing of the eye data and the providing of information about the at least one visible object are performed a plurality of times for different test persons, wherein each test person comprising a predefined state, especially a state of mind and/or an emotional state and or a state of attention, wherein in the set of task-specific control parameters is additionally derived in dependency of the predefined state. Therefore also the states of the test persons can additionally be taken into account and useful information can be derive therefrom.

According to another advantageous embodiment of the invention for deriving the set of task-specific control parameters an adaptive method is applied, especially machine learning, a neural network training, a statistical method or functional analytics. Such adaptive methods are especially advantageous when capturing data from different test persons or plurality of times for deriving the set of task-specific control parameters.

According to the second aspect of the invention it is advantageously possible to determine the set of rules and the relevant scene data based on analysis of a number of performances of the intended procedure by users with all skill levels and performance outcomes. This can be done analytically, statistically, or via machine learning approaches, using eye tracker data, scene video data and process result and performance data as inputs to determine the scene data and the set of rules relevant to be observed and controlled for, in order to achieve intended process results and performance.

This second aspect of the invention also relates to a system for providing a set of task-specific control parameters according to which a workflow comprising at least one task to be performed by a user is controlled. The system comprises a capturing device, like an eye tracker, for capturing eye data of at least one eye of a test person while the test person is performing the task. Furthermore, the system comprises a device, like a scene camera, for providing information about at least one visible object in the environment of the test person, in which the test person is performing the task. Moreover, the system comprises a processing unit, e.g. a micro-controller, configured to derive from the information about the at least one object and the eye data information about the behavior of the test person performing the task with regard to the environment of the test person and to derive therefrom task-specific control parameters, according to which the workflow comprising the at least one task is controlled for the user, wherein the task-specific control parameters at least specify a task condition, which specifies whether the task had been performed and/or whether the task is allowed to be performed.

The advantages described with regard to the method for providing a set of task-specific control parameters according to the second aspect of the invention and its embodiments correspondingly apply to the system for providing a set of task-specific control parameters according to the second aspect of the invention. Moreover, the features and preferred embodiments described with regard to the method providing a set of task-specific control parameters according to the second aspect of the invention constitute further preferred embodiments of the system for providing a set of task-specific control parameters according to the second aspect of the invention.

Furthermore, the preferred embodiments and features of the method and system to control a workflow according to the first aspect of the invention can also be combined with the method and system for providing a set of task-specific control parameters according to the second aspect of the invention and its embodiments and features thereof.

Further features of the invention and advantages thereof derive from the claims, the figures, and the description of the figures. All features and feature combinations previously mentioned in the description as well as the features and feature combinations mentioned further along in the description of the figures and/or shown solely in the figures are not only usable in the combination indicated in each place but also in different combinations or on their own. The invention is now explained in more detail with reference to individual preferred embodiments and with reference to the attached drawings.

Figure 2:
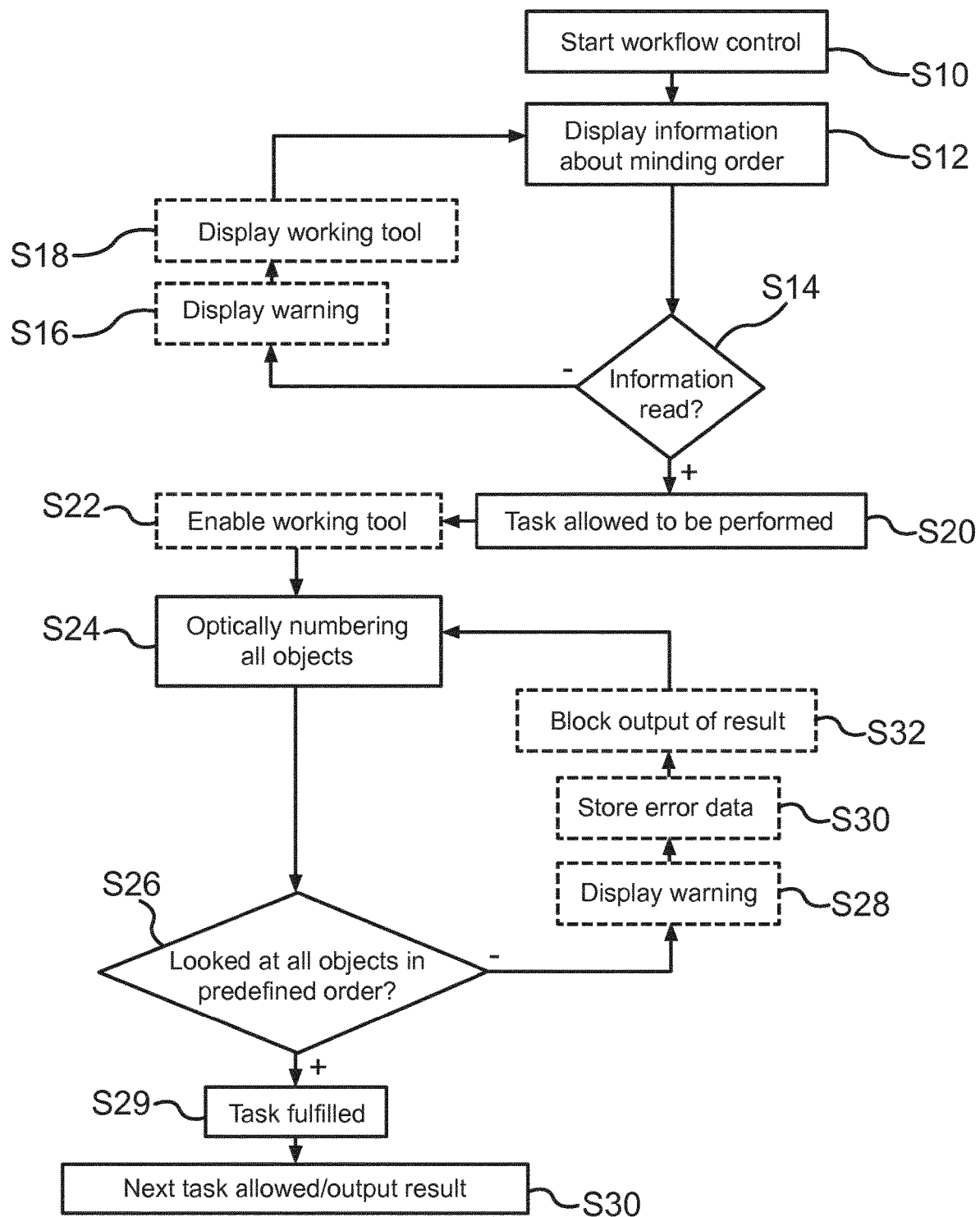
Figure 3:
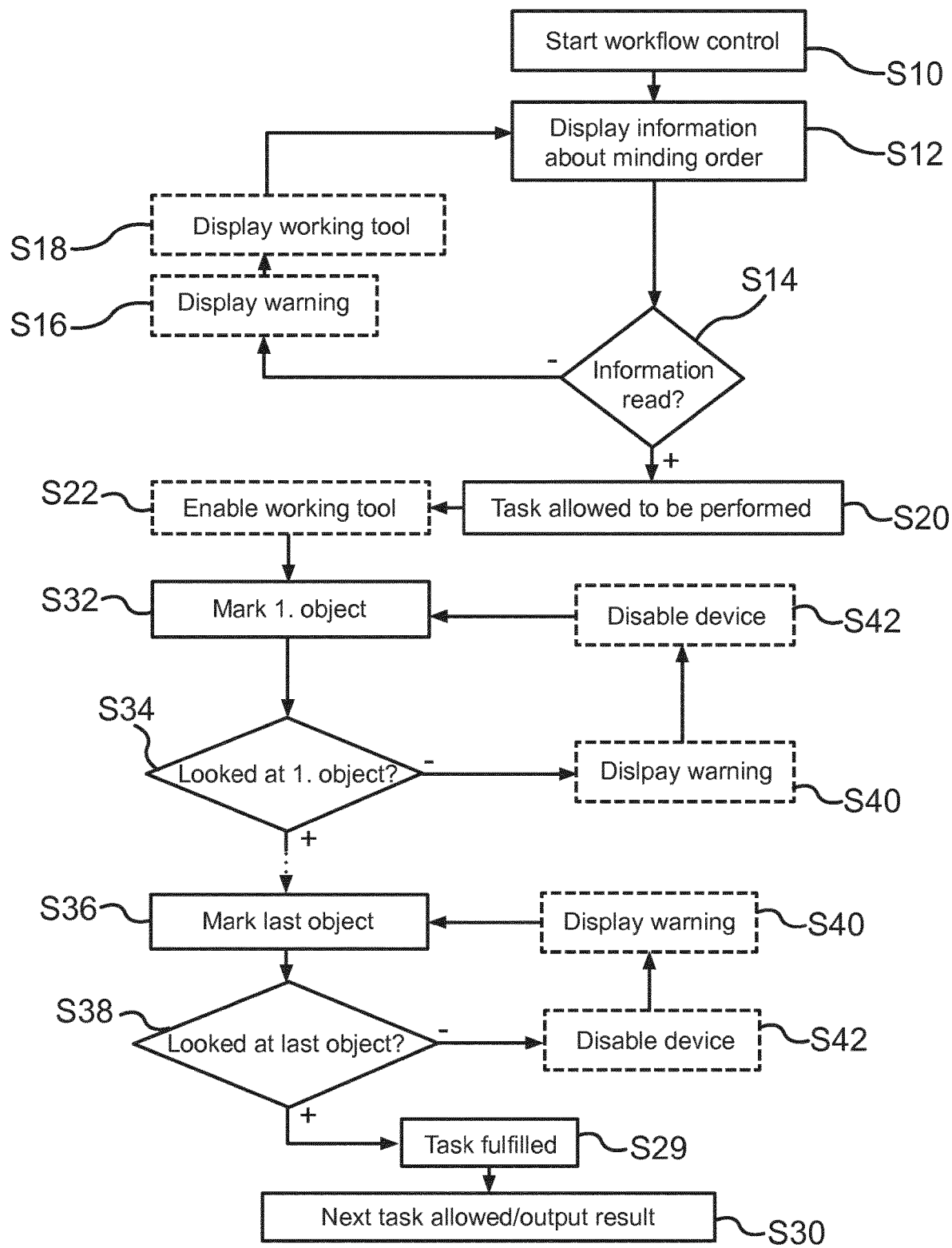
Figure 4:
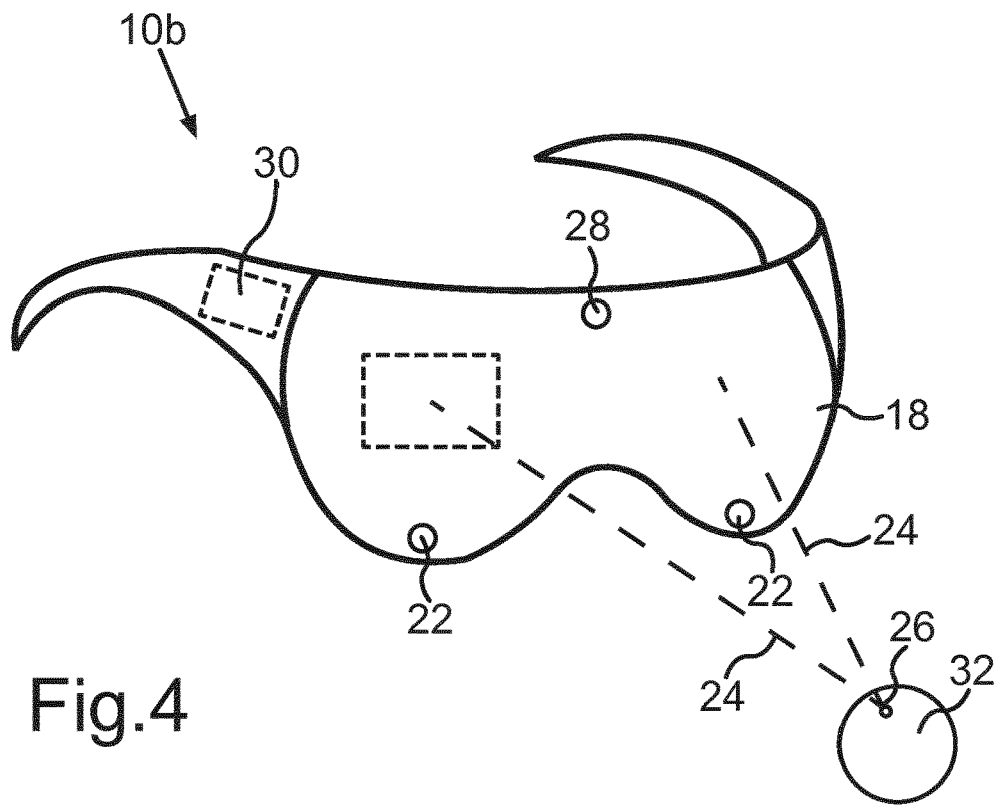
Figure 5:
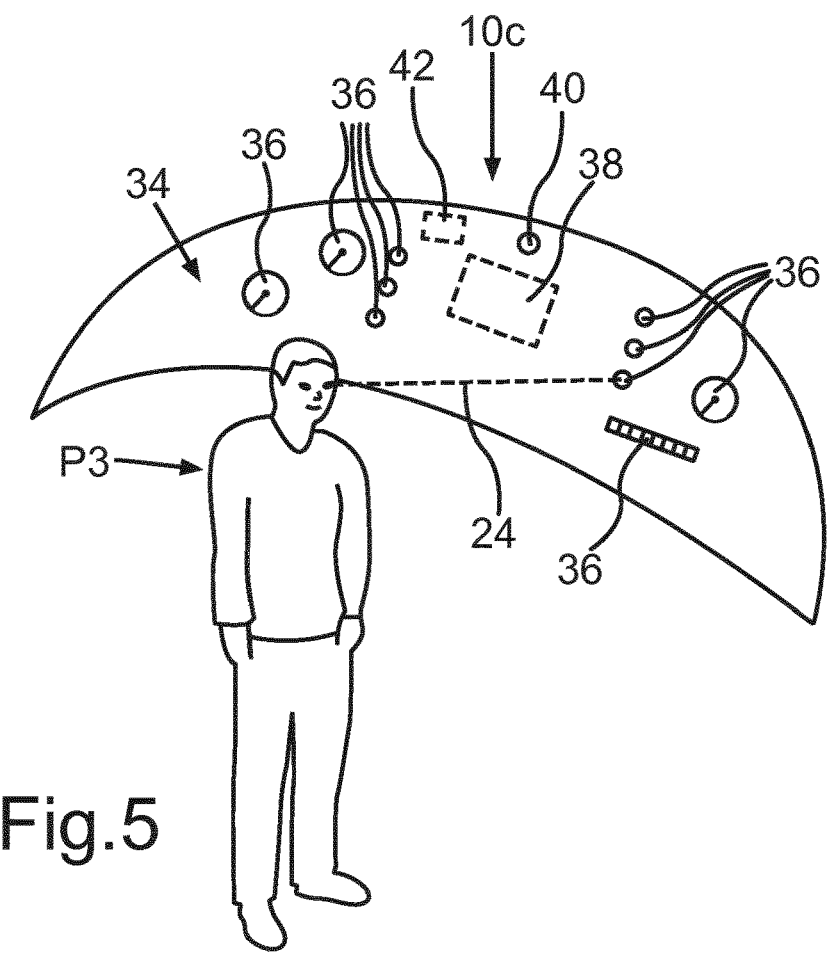

These show in:

FIG. 1 a schematic illustration of a system and method for providing a set of task-specific control parameters, according to which a workflow comprising at least one task to be performed by a user is controlled, according to an embodiment of the invention;

FIG. 2 a flowchart for illustrating a method to control a workflow according to an embodiment of the invention;

FIG. 3 a flowchart for illustrating a method to control a workflow according to another embodiment of the invention;

FIG. 4 a schematic illustration of a system to control a workflow according to an embodiment of the invention; and FIG. 5 a schematic illustration of a system to control a workflow according to another embodiment of the invention.

FIG. 1 shows a system 10a for performing a method for providing a set of task-specific control parameters CP, according to which a workflow comprising at least one task to be performed by a user is controlled, according to an embodiment of the invention. The system 10a may comprise one or more head-mounted devices 12, each comprising a scene camera 12a and eye cameras 12b as a part of respective eye trackers integrated into the head-mounted devices 12. Furthermore, the system 10a comprises a processing unit 14, which can be provided with a neural network 14a, to calculate the control parameters CP, which can be stored in a storage device 16 of the system 10a.

To provide the set of task-specific control parameters CP one or more test persons P1, P2 can wear the head-mounted devices 12 during they are performing a specific task of a workflow. While these test persons are performing this task, the respective scene cameras 12a capture a plurality of scene images in form of a scene video of the environment of the test persons P1, P2, in which these test persons P1, P2 are performing the task. On the basis of the captured scene images information about objects in the environment of the test persons P1, P2 can be provided. These captured scene images can then be provided in form of scene data S1, S2 to the processing unit. At the same time, namely when the test persons P1, P2 are performing the task, the eye cameras 12b capture eye data of the respective eyes of the test persons P1, P2, especially in the form of eye images, on the basis of which an eye tracker can calculate the respective gaze directions of the test persons P1, P2. These gaze directions or the eye data E1, E2 in general, can also be provided to the processing unit 14. The captured eye data E1, E2 can be set in relation to the respective scene data S1, S2 to derive for example information about at what point of the environment of the respective test person P1, P2 the test person P1, P2 was looking at a certain time, especially a respective gaze point with regard to the environment of the test person P1, P2 for each captured scene image can be calculated.

The objective of this method is to find out for example, which objects in the environment of a person P1, P2 are relevant objects for performing the certain task, whether there is a relevant timely order of single steps of the certain task, or whether single steps of a task have to be performed within certain time intervals, whether certain steps have to be repeated, especially more often than other steps, and so on. Now all this information can advantageously be derived from the scene data S1, S2 and the eye data E1, E2. For this purpose it is very advantageous if the scene data S1, S2 and the eye data E1, E2 are not only captured for one single performance of a certain task but also for a plurality of performances of one and the same certain task, either by one and the same test person P1, P2 or a plurality of different test persons P1, P2, at the same time or subsequently.

Objects in the environment of the test persons P1, P2, which can be identified for example on the basis of well known object detection algorithms, can be for example identified as relevant objects for the certain tasks if these objects have been looked at a minimum number of times and/or for a certain minimum time duration and so on. Also objects can be identified as relevant objects if the person P1, P2 was fixating them for a minimum time duration.

To verify such results, the results can be compared with each other. If for example an object was identified as a relevant object on the basis of the scene and eye data S1, E1 of a first person P1 and the same object was also identified as being a relevant object according to the scene and eye data S2, E2 of all other test persons P2, then this object can be classified to be a relevant object with high reliability. If this object, however, was identified only once to be a relevant object, then it probably was looked at the minimum number of times or for the certain minimum time duration unintentionally.

The same applies to deriving information about whether the timely order of performing single steps of the task is relevant or not. This for example can be assessed on the basis of whether objects have been looked at in a certain timely sequence for a minimum number of times for a number of repetition of the task or number of test persons.

Also additional information can be used when determining the control parameters CP, like information about the skill level SL of a respective test person P1, P2, as well as a quality level RQ of an outcome or result of the task. The skill level SL of the respective test persons P1, P2 and/or the result qualities RQ can be rated and inputted into the system 10a manually or rated by the system 10a itself. This way for example the input data of the respective test person P1, P2 can then be weighted according to their respective skill levels SL. Also respective weight can be applied depending on the result quality RQ. Also further information about the specific task can be derived like whether there are correlations between the duration of looking at an object and a better result, or looking at a certain object more often and a better result. Similarly, it can be determined whether performing certain steps of the task within time limits is relevant or not, or whether time limits or time intervals are important or not.

By means of an analysis of these data, namely the scene data S1, S2, the eye data E1, E2 and optionally respective skill levels SL and result qualities RQ, the control parameters CP for a specific task can be derived and be stored in the storage device 16. These control parameters CP therefore can specify for example a task condition, which itself specifies whether this task had been performed and/or whether the task is allowed to be performed, for example on the basis of the identification of objects as being relevant for the task and other criteria explained above.

These task-specific control parameters CP can then advantageously be used for controlling a workflow comprising this specific task to be subsequently performed by any other user.

Moreover, the processing unit 14 can also use other methods for deriving the control parameters CP besides neural networks 14a, like other adaptive methods for example statistical methods or functional analytics.

FIG. 2 shows a flowchart for illustrating a method to control a workflow according to an embodiment of the invention. This workflow comprises at least one task, for which it has been determined, for example by means of a method described with regard to FIG. 1, that a certain number of objects in the environment of the person, who has to perform the task, are relevant, wherein furthermore these relevant objects can be assigned to single steps of the task in a timely order, which is relevant as well. An example of such a task could be for example that a worker has to tighten a certain number of screws in predefined order on a workpiece. Another example could be a person has to make coffee with a coffee machine and has to fill in water into the water tank before pressing the button for activation of the coffee machine.

The method starts in S10 with a start of the workflow control. After that, information can be displayed to the person on any kind of display device in S12 informing him/her that he has to take care of the timely order, in which single steps have to be performed. After that in S14 it can be checked whether the person had read the information or not. This can be done for example by comparing captured points of regard of the person with the position, in which the information in S12 is displayed. If the person has not read the information, optionally a warning information can be displayed in S16, especially on any kind of displaying device, and/or a working tool like an electric screw driver or a coffee machine in above-named examples, can be blocked or the activation can be prohibited in S18. Moreover, as long as the person has not read the information the information about minding the order of steps keeps being displayed. If it is recognized in S14 that the person had read the information, then the task is allowed to be performed in S20. Reading the displayed information therefore constitutes the task condition defining whether the task is allowed to be performed or not. So, if now the task is allowed to be performed, optionally a working tool, like the above-named, can be enabled in S22 and moreover guidelines can be provided for the person in S24 giving further advice of how to perform the task. For example, all relevant objects relating to the task can be optically marked or highlighted, for example by means of augmented reality glasses, by means of which such additional information can be overlaid over the respective environment of the person. Also numbers can be displayed defining the order, in which the person has to use the relevant objects. For example, if the person looks at the screws, these can be numbered by means of the augmented reality device to show in what order the person has to tighten them on the workpiece. If the user looks at the coffee machine, also the water tank and the press button can be numbered correspondingly. The displaying of the numbers in their correct positions relative to the respective objects of the environment can again be derived from scene images of a head-mounted device in combination with object recognition algorithms. Then again in S26 gaze data of the user are additionally used to check whether the person has looked at all the relevant objects, especially in the predefined order. So in case the person missed to look at a certain object or looked at all of these objects but not in the correct order, optional consequences may be for example displaying a warning to the person in S28 and storing the error data about having detected that the task was not performed correctly, for example in a storage device in S30 and/or blocking the output of a result of the task in S32. By displaying a warning the person can advantageously be informed that he has not performed the task correctly, storing error data is very advantageous for failure analysis and by blocking the output of a result on the one hand the person again can notice that something is wrong and he has not performed the task correctly and on the other hand further negative consequences of the task being performed incorrectly can be avoided, like overheating the coffee machine when brewing coffee without having water in the water tank.

If, however in S26 it is determined that a person has looked at all relevant objects in the predefined order, the task is considered to be fulfilled in S29, meaning that a second task condition consisting in whether the task had been performed is fulfilled. This procedure can be performed again for every single task of a workflow, if a workflow comprises several tasks. Also the next task of a workflow might only be allowed, if the previous task is considered to be fulfilled. So in this case, either in S30 the next task is allowed to be performed or alternatively the result of the task or the workflow is outputted.

FIG. 3 shows a flowchart for illustrating a method to control a workflow according to another embodiment of the invention. This method is at the beginning identical to the method already explained with regard to FIG. 2. However, in this case, after the task is considered to be allowed to be performed in S20 and optional a working tool is enabled in S22, only the first relevant object of the plurality of relevant objects according to the predefined order is optically marked by display means, like augmented reality glasses in S32. After that in S34 it is checked whether the person has looked at the first object or not. If it is determined that the person has looked at the first object the same procedure can be repeated with regard to the second object, a third object and so on until the last object, which is marked in S36. Again, in S38 it is checked whether the person has looked at the last object. If, however, it is determined in S34 or S38 or in any intermediate step for checking whether the person had looked at the object of the relevant number, that a person has not looked at the object, the respective object can stay marked until the person has. Moreover, optionally again a warning can be displayed to the person informing him/her that the task is not fulfilled yet in S40 and also optionally a device the person is working with or has to perform the task with can be disabled in S42. If finally all these conditions are fulfilled, namely the person has looked at each object in the predefined order task is again considered to be fulfilled in S29 and the next task may be allowed or a result may be outputted in S30.

FIG. 4 shows a schematic illustration of a system 10b to control a workflow according to an embodiment of the invention. In this case the system 10b is configured as a head-mounted device. This head-mounted device can for example be an augmented reality device having see-through displays, on which additional content can be displayed like a display of a task information 20. Moreover, 10b comprises an eye-tracking device having eye cameras 22 for capturing images of the eyes of the person wearing the head-mounted device. On the basis of the captured eye images gaze direction 24 of the person or also the point of regard 26 can be calculated. Furthermore, the head-mounted device comprises a scene camera 28, which is configured to capture images of the environment of the person. These scene images as well as the eye images can then be processed and analyzed by means of a processing unit 30 which can also be integrated in the head-mounted device. On the basis of the scene images, the processing unit 30 can, for example by means of known object recognition techniques, identify certain objects 32 in the environment of the person. Also, the processing unit 30 can determine additionally on the basis of the captured eye images and the gaze direction 24 and a point of regard 26 derived therefrom, whether the person is looking at such a certain object 32 or not, especially also how long or when. Furthermore, the processing unit 30 can also determine whether the person is looking at the task information 20 displayed on the see-through displays 18 or not. This can be for example done again on the basis of the captured gaze direction 24 and the known position of the displayed task information 20. This system 10b can for example be used for performing a method described with regard to FIG. 2 or FIG. 3. Based on the captured scene images, the information about the displayed task information 20 and the eye images the processing unit 30 can determine whether certain task conditions are fulfilled consisting in for example whether the task has been performed, for example by detecting that the person has looked at the relevant object 32 and/or consisting whether the task is allowed to be performed, for example when it is detected that the person has read the displayed task information 20. The head-mounted device can also be configured to output warnings on the displays 18, e. g. if certain conditions are not fulfilled or the task had not been performed correctly. The processing unit 30 may also be communicatively coupleable to other devices like working tools to provide control signals, for example to block functions or disable the working tool, and so on, if certain conditions are not fulfilled, like certain steps have not been performed correctly by the person.

FIG. 5 shows another schematic illustration of a system 10b to control a workflow according to another embodiment of the invention. In this case the system is not configured as head-mounted device, instead it is integrated in an inner control panel. This control panel 34 may have several instruments or displays, lamps, and so on. These components of the panel 34 are uniformly denoted as 36. The panel 34 may also have a central monitor 38 for displaying certain information. The task a person P3 now has to perform may be for example scanning all the instruments 36 and/or the monitor 38 every thirty seconds. The system 10c for controlling this workflow comprises in this example a remote eye tracker with a camera 40 and a processing unit 42. The processing unit 42 can analyze the images captured by the camera 40 and therefrom derive the position and gaze direction 24 of the person P3. Moreover, the positions of the respective instruments 36 and the central monitor 38 are also known to the processing unit 42, e. g. saved in a storage device. The processing unit 42 can calculate on the basis of the calculated gaze direction whether the point of regard of the user coincides with the respective positions of the instruments 36 or the central monitor 38. On the basis of this information the processing unit can check whether the user is looking at the instruments and/or the central monitor 38 or not, and even on which of them or also within predefined time intervals. The processing unit 42 can also be coupled to the central monitor 38 to provide additional task information to the person P3 or to output warning information if the person P3 forgets to check all the instruments 36 regularly.

Therefore, by means of the invention attention aware workflow control can be provided that determines tasks and/or steps based on the user acknowledging instructions or warnings and/or the coverage of certain visual spaces or objects. Also different control models can be provided like a sequence control, e.g. gaze-based enforcing of workflows according which the next step is only allowed to be executed if a certain gaze pattern was performed, which is the indicator for the user acknowledging an event or instruction or having seen the critical information or done the required steps, as well as completion control, where for example a result or an interim result or a diagnosis or action can only be issued or taken if a certain set of visual intakes has been covered, i. e. if all objects in a piece of luggage of the display of a luggage scanner have been fixated or all areas of certain level of intensity change in a mammographic x-ray images have been looked at, or a helicopter pilot has scanned all instruments every x seconds.

The invention combines gaze information, visual subject matter information with a set of rules to control a process that has one or several overarching objectives. These methods and systems involve preferably eye tracker, a scene camera, a data base with scene data, algorithms to detect scene data in scene video and gaze in scene and on scene data and a set of rules for compliance and control of the visual and actual process. Such a set of rules can also be determined in the relevant scene data based on analysis of a number of performances of the intended procedure by users without skill levels and performance outcomes. This can be done analytically, statistically, or via machine learning approaches using eye tracker data, scene video data and process result and performance data as inputs to determine the scene data in the set of rules relevant to be observed and controlled for in order to achieve intended process results and performance. This enables to establish guidelines in order to ensure high quality and to protect a worker or user in dangerous situations or processes. Often guidelines are not followed out of convenience, however, the here suggested system and method helps to enforce appropriate visual intakes of the user and persons to avoid critical omissions in perception or decision-making. If only results of procedures were controlled for, it remains unknown which visual input has been missed by the user, leading to an intended result by chance and thereby having an unstable process or if the intended result is not achieved the cause remains hidden. This is even more critical, when the result can be observed only a long time later or when it is too late or has become very costly to correct. This is typical e. g. in medical screening and diagnostic procedures or in preventive quality inspection tasks. In these cases, the process itself ensures the quality as the results and their correctness can only be assessed much later, often only after irreversible damage has occurred, which should have been prevented by the diagnostic or inspection procedure in the first place. However, the invention and its embodiments enable to observe and monitor each single step and the respective results of a procedure or process and especially detect when certain steps or tasks are not performed correctly. Therefore, errors or failure can be recognized right away or when the output of incorrect results can be effectively prevented. Also augmented reality systems can help untrained personal to do tasks which used to require a professional with enforcing certain sequences and/or coverage of visual intake. This can be realized more safely and with less liability. The same applies to the training of tasks where visual perception and feeding of mental is critical for high performance and good decision-making.

LIST OF REFERENCE SIGNS

10$a$, 10$b$, 10$c$ system
12 head mounted device
12$a$ scene camera
12$b$ eye camera
14 processing unit
14$a$ neural network
16 storage device
18 displays
20 task information
22 eye camera
24 gaze direction
26 point of regard
28 scene camera
30 processing unit
32 object
34 control panel
36 instrument
38 central monitor
40 camera
42 processing unit
P1, P2 test person
P3 person
S1, S2 scene data
E1, E2 eye data
SL skill level
RQ result quality
CP task-specific control parameters

The invention claimed is:

1. A method comprising:
capturing an image of the eye of a user;
determining a gaze direction of the user based on the image of the eye of the user;
determining, based on the gaze direction, that the user has inspected a plurality of objects in a predefined order; and
in response to determining that the user has inspected the plurality of objects in the predefined order, enabling a device to allow the user to perform a task associated with the plurality of objects.

2. The method of claim 1, further comprising:
determining a state of attention of the user based on the image of the eye of the user; and
determining, based on the state of attention, that the user has attentively inspected the plurality of objects,
wherein the device is enabled in response to determining that the user has attentively inspected the plurality of objects.

3. The method of claim 1, further comprising:
determining that the user has inspected the plurality of objects within a predefined time interval,
wherein the device is enabled in response to determining that the user has inspected the plurality of objects within the predefined time interval.

4. The method of claim 1, wherein the plurality of objects includes at least one object in the environment of the user.

5. The method of claim 1, wherein the plurality of objects includes at least one object in an image presented to the user.

6. The method of claim 5, wherein the object in the image presented to the user includes task information regarding the task.

7. The method of claim 1, wherein determining that the user has inspected the plurality of objects includes comparing the gaze direction with position information of the certain object.

8. The method of claim 7, further comprising:
capturing an image of an environment of the user;
determining, based on the image of the environment of the user, the position information of the plurality of objects.

9. The method of claim 1, wherein the device includes a working tool.

10. An apparatus comprising:
a camera configured to capture an image of the eye of a user;
a communications interface configured to communicate with a device; and
a processor configured to:
determine a gaze direction of the user based on the image of the eye of the user;
determine, based on the gaze direction, that the user has inspected a plurality of objects in a predefined order; and
in response to determining that the user has inspected the plurality of objects in the predefined order, transmit, via the communications interface, a control signal enabling the device to allow the user to perform a task associated with the plurality of objects.

11. The apparatus of claim 10, wherein the processor is further configured to:
determine a state of attention of the user based on the image of the eye of the user; and
determine, based on the state of attention, that the user has attentively inspected the plurality of objects,
wherein the control signal enabling the device is transmitted in response to determining that the user has attentively inspected the plurality of objects.

12. The apparatus of claim 10, wherein the plurality of objects includes at least one object in the environment of the user.

13. The apparatus of claim 10, further comprising a display to present a display image to the user, wherein the plurality of objects includes at least one object in the display image.

14. The apparatus of claim 13, wherein the object in the display image includes task information regarding the task.

15. The apparatus of claim 10, further comprising a scene camera to capture an image of an environment of the user, wherein the processor is further configured to:
determine, based on the image of the environment of the user, position information of the plurality of objects; and
determine that the user has inspected the certain object by comparing the gaze direction with the position information of the plurality of objects.

16. A non-transitory computer-readable medium encoding instructions which, when executed, cause a processor to perform operations comprising:
capturing an image of the eye of a user;
determining a gaze direction of the user based on the image of the eye of the user;
determining, based on the gaze direction, that the user has inspected a plurality of objects in a predefined order; and
in response to determining that the user has inspected the plurality of objects in the predefined order, enabling a device to allow the user to perform a task associated with the plurality of objects.

17. The non-transitory computer-readable medium of claim 16, the operations further comprising:
determining a state of attention of the user based on the image of the eye of the user; and
determining, based on the state of attention, that the user has attentively inspected the plurality of objects t,
wherein the control signal enabling the device is transmitted in response to determining that the user has attentively inspected the plurality of objects.

18. The non-transitory computer-readable medium of claim 16, the operations further comprising presenting a display image to the user, wherein the plurality of objects includes at least one object in the display image including task information regarding the task.

19. The non-transitory computer-readable medium of claim 16, the operations further comprising:
capturing an image of an environment of the user; and
determining, based on the image of the environment of the user, position information of the plurality of objects,
wherein determining that the user has inspected the plurality of objects includes comparing the gaze direction with the position information of the plurality of objects.

* * * * *